United States Patent [19]
Ericson et al.

[11] Patent Number: 6,139,748
[45] Date of Patent: Oct. 31, 2000

[54] METHOD AND DEVICE FOR MONITORING AN INFUSION PUMP

[75] Inventors: Björn Ericson, Lund; Olle Esser, Malmö, both of Sweden

[73] Assignee: Gambro AB, Sweden

[21] Appl. No.: 09/157,690

[22] Filed: Sep. 21, 1998

[30] Foreign Application Priority Data

Sep. 22, 1997 [SE] Sweden ................................ 9703403

[51] Int. Cl.[7] ................................................ B01D 61/20
[52] U.S. Cl. .................... 210/646; 210/87; 210/321.65; 210/929; 210/433.1; 604/67; 73/1.16
[58] Field of Search ................................ 210/87, 321.65, 210/321.71, 646, 647, 739, 929, 433.1; 604/4–6, 65, 67; 73/1.16, 1.57, 861

[56] References Cited

U.S. PATENT DOCUMENTS

| | | | |
|---|---|---|---|
| 4,585,552 | 4/1986 | Gummesson et al. | 210/87 |
| 4,784,495 | 11/1988 | Jonsson et al. | 366/151 |
| 4,844,810 | 7/1989 | Richalley et al. | 210/646 |
| 4,923,598 | 5/1990 | Schäl | 210/87 |
| 5,366,630 | 11/1994 | Chevallet | 210/646 |
| 5,578,223 | 11/1996 | Bene et al. | 210/646 |
| 5,733,257 | 3/1998 | Sternby | 604/67 |
| 5,792,367 | 8/1998 | Mattison et al. | 210/646 |

FOREIGN PATENT DOCUMENTS

| | | | |
|---|---|---|---|
| 516152 | 12/1992 | European Pat. Off. | 604/65 |
| 95/10310 | 4/1995 | WIPO . | |

OTHER PUBLICATIONS

Patent Abstracts of Japan, 1–303157, Japanese Application No. 63–134142, Satoshi Shiroi, Method of Calibrating Dialysis Device, Dec. 7, 1989.

*Primary Examiner*—Joseph W. Drodge
*Attorney, Agent, or Firm*—Lerner, David, Littenberg, Krumholz & Mentlik, LLP

[57] ABSTRACT

Methods and apparatus are disclosed for monitoring an infusion pump utilized in a dialysis machine for hemodiafiltration or hemofiltration. The apparatus includes a first flow circuit for a dialysis solution, including a flow meter, a second flow circuit for blood, the dialysis apparatus including a first chamber connected to the first flow circuit, a second chamber connected to the second flow circuit, and a semipermeable membrane separating the first and second chambers, a third flow circuit for withdrawing an infusion solution from the first flow circuit and delivering the infusion solution to the second flow circuit, the third flow circuit including the infusion pump, and a first valve for disconnecting the dialysis apparatus from the first flow circuit and connecting the infusion pump in series with the flow meter in the first flow circuit whereby the expected flow through the infusion pump can be compared with the measured flow through the flow meter.

9 Claims, 4 Drawing Sheets

METHOD AND DEVICE FOR MONITORING AN INFUSION PUMP

FIELD OF THE INVENTION

The present invention relates to a method and apparatus for monitoring an infusion pump in dialysis apparatus such as a hemodiafiltration or a hemofiltration machine. More particularly, the present invention relates to a method and apparatus for calibrating the infusion pump.

BACKGROUND OF THE INVENTION

A conventional type of hemodialysis machine is disclosed in European Patent No. 278,100. Such a dialysis machine is marketed under the tradename GAMBRO AK 200 ULTRA and is adapted to perform hemodialysis, hemodiafiltration or hemofiltration treatments.

The dialysis machine prepares a dialysis solution comprising sodium, bicarbonate, potassium, calcium, magnesium, chloride and acetate ions in suitable concentrations, as well as possibly glucose and other ions, all dissolved in water. The concentrations of the ions in the dialysis solution are generally mirror images of their concentrations in blood, where the optimum is the normal concentration of these ions in blood. Thus, if the concentration of an ion is increased in the blood over its normal concentration, the ion concentration in the dialysis solution is decreased in relation to the normal concentration. The pH of the solution is adjusted to about 7.1–7.4.

During hemodialysis treatment, the solution is used to achieve dialysis in a dialyser. The dialyser is divided into two chambers by means of a semi-permeable membrane. Blood which is to be treated passes over one side of the membrane while the dialysis solution prepared by the dialysis machine passes over the other side. Diffusion of ions takes place through the membrane in order to condition the blood and to at least partially replace the function of the kidneys. In addition, a quantity of liquid is removed from the blood since the patient is unable to get rid of surplus liquid in the normal manner. This removed liquid flowing through the membrane is called the ultrafiltrate flow.

During hemodiafiltration, the ultrafiltrate flow is increased above that which is necessary to restore the liquid balance of the patient. As replacement, an infusion solution is thus added to the blood in order to permit such increased ultrafiltration flow.

During hemofiltration, substantially no dialysis takes place, but instead the blood is filtered, whereby a portion of the ultrafiltration volume is added to the blood as an infusion solution. The difference between the ultrafiltration volume and the added substitution volume constitutes the volume of liquid which is removed from the patient in order to restore the liquid balance. The infusion solution may be added upstream of the dialyser or hemofilter in a process called "pre-infusion", or downstream of the dialyser or hemofilter in a process called "post-infusion".

In order to effect the infusion flow, the dialysis machine includes an infusion pump which is connected to an outlet for infusion solution on the dialysis machine. The infusion solution is normally the same as the dialysis solution. The infusion solution passes through the infusion pump, and a sterile filter, and is then fed to the patient's blood. The infusion pump may be a so-called peristaltic pump, as is used in the above-mentioned GAMBRO AK 200 ULTRA dialysis machine.

Prior to treatment, the dialysis machine is provided with a tube set, the constituent components of which must be filled with liquid so that all air is expelled. This normally takes place in a priming step during which sterile sodium chloride solution is fed into the various tubes and components of the tube set. The conduit system of the dialysis machine is also filled with dialysis solution.

During priming of the infusion circuit, a dedicated deaeration conduit from the sterile filter is used in order that the filter may be completely filled with priming liquid so that air is expelled. The nurse generally uses forceps or a tube clamp, which is placed on the normal output conduit from the sterile filter and thereby cuts off the flow therethrough. In addition, a tube clamp is opened in the deaeration conduit from the sterile filter. After deaeration of the sterile filter, the nurse removes the forceps from the output conduit or opens the tube clamp, as well as closing the tube clamp on the deaeration conduit, and the priming continues.

Due to the human factor, the nurse may forget to remove the forceps or to open the tube clamp, which may result in no infusion taking place. This may have serious consequences for the treatment if it is not corrected.

The infusion pump may be a peristaltic pump which is driven at a predetermined speed or number of revolutions so that a desired infusion flow or volume is attained. However, such peristaltic pumps are sensitive to the pressure at the inlet, and it may therefore be desirable to calibrate the pump for the particular treatment and/or to check whether the desired infusion volume has actually being attained at a particular rotational speed of the peristaltic pump.

A peristaltic pump may exhibit leakage due to the fact that occlusion of the pump segment is not complete, which may result in zero flow.

In addition, problems may arise if the user installs a tube set which is not intended for the dialysis machine in question, for example a counterfeit copy, which may not provide a suitable infusion flow.

It may also be desirable to indicate if all air in the sterile filter has been completely expelled during priming, or if there is a blockage or leakage in the sterile filter.

One object of the present invention is to provide a method and apparatus for permitting detection of the above-mentioned operational faults.

A further object of the present invention is to provide a method and apparatus of the above-mentioned type in which substantially only components which normally form a part of a dialysis machine are used.

SUMMARY OF THE INVENTION

In accordance with the present invention, these and other objects have now been realized by the invention of a method for monitoring an infusion pump utilized in dialysis apparatus comprising flowing a dialysis solution through a first flow circuit including a flow meter, flowing blood through a second flow circuit separated from the first flow circuit by a semipermeable membrane in the dialysis apparatus, providing an infusion solution from the first flow circuit to the second flow circuit by means of an infusion pump, disconnecting the dialysis apparatus from the first flow circuit, and flowing a fluid through the flow meter and through the infusion pump for comparing the expected flow through the infusion pump with the measured flow to the flow meter. In a preferred embodiment, the dialysis apparatus is a dialyser or a hemofilter.

In accordance with one embodiment of the method of the present invention, the flow meter comprises a first flow meter portion for measuring incoming flow into the first flow circuit and a second flow meter portion for measuring outgoing flow out of the first flow circuit, the first flow meter portion being connected in series with the infusion pump. Preferably, the method includes flowing the fluid through the first flow circuit and bypassing the dialysis apparatus, and determining the difference between the incoming flow in the first flow meter portion and the outgoing flow in the second flow meter portion.

In accordance with the apparatus of the present invention, apparatus has been provided for monitoring an infusion pump in dialysis apparatus comprising a first flow circuit for a dialysis solution, the first flow circuit including a flow meter, a second flow circuit for blood, the dialysis apparatus including a first chamber connected to the first flow circuit, the second chamber connected to the second flow circuit, and a semipermeable membrane separating the first and second chambers, a third flow circuit for withdrawing an infusion solution from the first flow circuit and delivering the infusion solution to the second flow circuit, the third flow circuit including the infusion pump, and a first valve for disconnecting the dialysis apparatus from the first flow circuit and connecting the infusion pump in series with the flow meter in the first flow circuit whereby the expected flow through the infusion pump can be compared with the measured flow through the flow meter. Preferably, the dialysis apparatus is a dialyser or a hemofilter.

In accordance with one embodiment of the apparatus of the present invention, the first valve is connected in the first flow circuit upstream of the dialyser whereby when the first valve disconnects the dialyser apparatus from the first flow circuit all flow through the flow meter also passes through the infusion pump. In a preferred embodiment, the flow meter comprises a first flow meter portion for measuring incoming flow into the first flow circuit and a second flow meter portion for measuring outgoing flow out of the first flow circuit, the first flow meter portion being connected in series with the infusion pump. In accordance with a preferred embodiment, the first valve is located in the first flow circuit at a predetermined location for disconnecting the dialyser from the first flow circuit, and the apparatus includes a bypass conduit and a second valve for continuing the flow through the first flow circuit through the bypass conduit, whereby the expected flow through the infusion pump can be compared with the difference between the incoming and outgoing flows through the flow meter. In a preferred embodiment, the apparatus includes an ultrafiltration pump for supplying a fluid to the first flow circuit whereby the inlet flow from the ultrafiltration pump into the first flow circuit and the outlet flow out of the first flow circuit from the infusion pump can be equalized.

In accordance with the present invention, a method is provided for monitoring an infusion pump in a machine for hemodiafiltration or hemofiltration. The machine comprises a first flow circuit for a dialysis solution, a flow meter arranged in the first flow circuit, a second flow circuit for blood, a dialyser or a hemofilter which, by means of a semi-permeable membrane, is divided into a first chamber connected to the first flow circuit and a second chamber connected to the second flow circuit, a third flow circuit from an outlet for infusion solution in the first flow circuit to a connection in the second flow circuit and comprising an infusion pump. The method comprises the steps of disconnecting the dialyser from the first flow circuit, connecting the infusion pump in series with the flow meter in the first flow circuit, and monitoring the infusion pump by comparing the expected flow through the infusion pump with the measured flow through the flow meter. In this manner, the infusion pump is calibrated with reference to the flow meter.

In a preferred embodiment of the present invention, the flow meter is constructed as a double flow meter having portions for measuring incoming and outgoing flows configured so that the flow meter portion for incoming flow is connected in series with the infusion pump. Alternatively, the flow meter may comprise an ultrafiltration metering pump.

As another alternative, the flow in the first flow circuit may bypass the dialyser or hemofilter by means of a bypass conduit, so that the flow meter determines the difference between incoming flow and outgoing flow in the first flow circuit.

In accordance with the present invention, there is also provided apparatus for monitoring an infusion pump in a machine for hemodiafiltration or hemofiltration. The machine comprises a first flow circuit for a dialysis solution, a flow meter arranged in said first flow circuit, a second flow circuit for blood, a dialyser or a hemofilter which, by means of a semi-permeable membrane, is divided into a first chamber connected to the first flow circuit and a second chamber connected to the second flow circuit, and a third flow circuit from an outlet for infusion solution from the first flow circuit to a connection in the second flow circuit, comprising an infusion pump. According to the present invention, the apparatus further comprises a first valve for disconnecting the dialyser from the first flow circuit and connecting the infusion pump in series with the flow meter in the first flow circuit, and an arrangement for monitoring the infusion pump by comparing the expected flow through the infusion pump with the measured flow through the flow meter.

In a preferred embodiment, the first valve is arranged in a conduit which connects the outlet with the dialyser so that the flow in the first flow circuit ceases and all flow through the flow meter also passes through the infusion pump.

Alternatively, the first valve can be arranged in a conduit which connects the dialyser with the first flow circuit so that the dialyser is completely disconnected from the first flow circuit, whereby a second valve connects the dialysis flow by means of a bypass conduit past the dialyser. An arrangement is also provided for monitoring the infusion pump by comparing the expected flow through the infusion pump with the difference between incoming and outgoing flows through the flow meter.

In another embodiment, the flow meter comprises an ultrafiltration pump which supplies liquid to the first flow circuit, such that the inlet flow and outlet flow in the first flow circuit are equal.

BRIEF DESCRIPTION OF THE DRAWINGS

Further objects, features, advantages and properties of the method and apparatus of the present invention will become apparent through the following detailed description, which refers to the drawings, in which.

DETAILED DESCRIPTION

Figure 1:
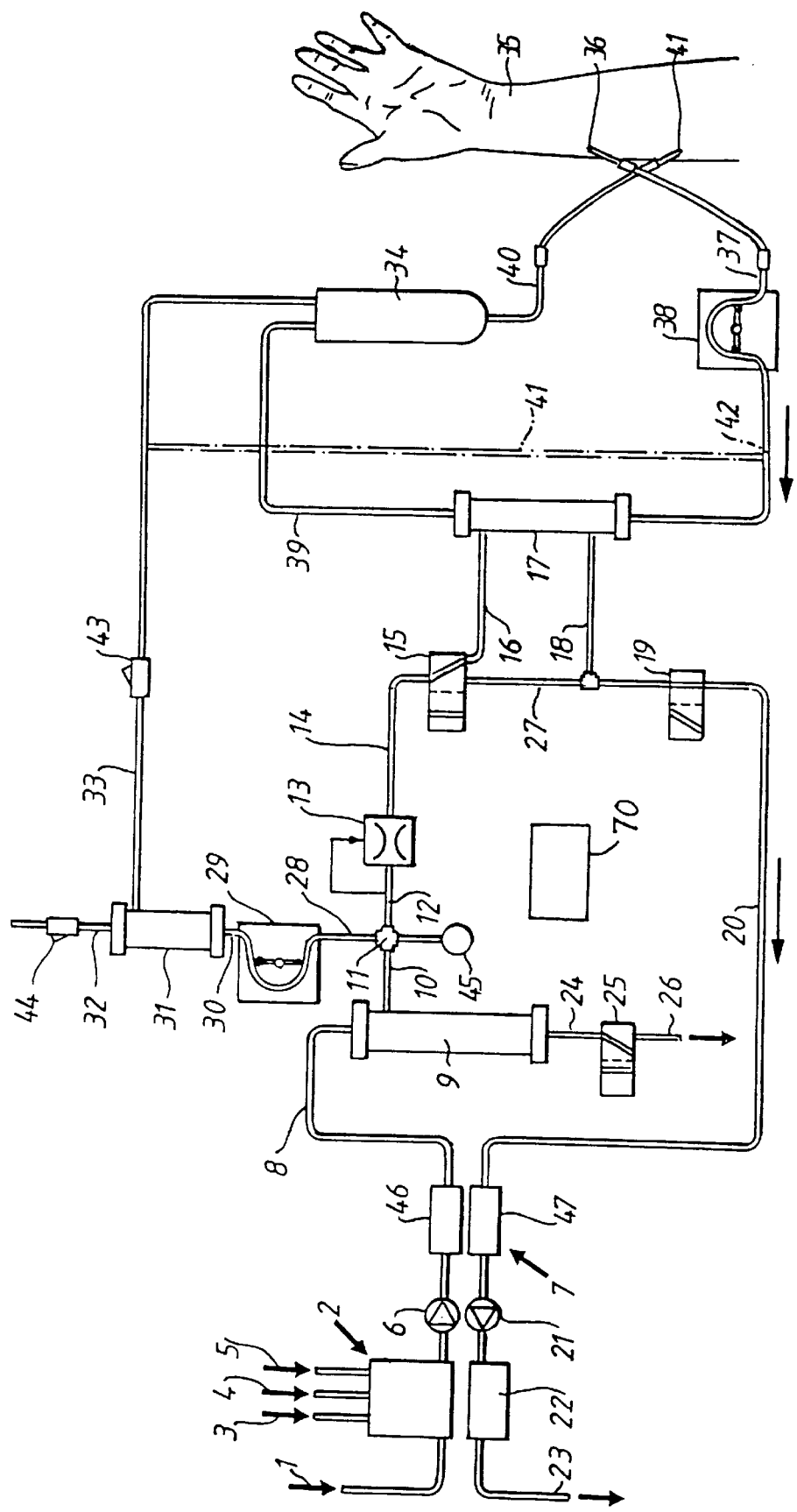
FIG. 1 is a schematic diagram of a conventional dialysis machine to which the present invention may be applied.

Turning to the drawings, in which like reference numerals refer to like elements thereof, FIG. 1 is a schematic diagram of a portion of a dialysis machine, for example of the GAMBRO AK 200 ULTRA type.

The dialysis machine shown in FIG. 1 comprises an inlet 1 for pure water, normally obtained from a reverse osmosis (RO) unit. In addition, a preparatory unit 2 is provided for the preparation of a dialysis solution of a desired composition from one or more concentrates, which are denoted by arrows 3, 4 and 5. The preparatory unit 2 is conventional and thus will not be described in further detail.

A pump 6 feeds the dialysis solution through a flow meter 7 and a first conduit 8 to a first filter 9. The filter 9 is a filter which is used for multiple treatments and has a large surface area. The filter 9 passes substances, molecules and ions below a certain predetermined size, for example below a diameter of about 5 nm.

The filtered dialysis solution flows along a conduit 10 to an outlet 11 from which an infusion solution may be removed. A conduit 12 extends from the outlet 11 to a throttle valve 13 which ensures that the pressure upstream of the throttle valve is substantially constant, for example +50 mmHg. A conduit 14 extends from the throttle valve 13 to a switching valve 15 and further through a tube 16 to a dialyser 17. A conduit 18 extends from the dialyser 17 to a valve 19. A conduit 20 extends from the valve 19 back to the flow meter 7. The dialysate flows through the flow meter and, by means of pump 21 and further devices 22, to an outlet 23.

The flow meter 7 consists of two portions or channels, 46 and 47, so that incoming and outgoing flow may be measured separately. In addition, an accurate value of the difference between the outgoing and incoming flows may be obtained, which difference normally corresponds to the ultrafiltrate flow which is removed in the dialyser 17.

A conduit 24 extends from the filter 9 through a valve 25 to an outlet 26.

A bypass conduit 27, which bypasses the dialyser 17, extends between valves 15 and 19.

A conduit 28 extends from the outlet 11 to a peristaltic pump 29 and further by means of a conduit 30 to a sterile filter 31. A conduit 32 for deaeration of the sterile filter is connected to the other end of the sterile filter 31. In addition, a conduit 33 is provided which extends from the sterile filter to a drip chamber 34. The sterile filter 31 is normally used once, and is generally sterilized before such use.

The dialysis machine also comprises an extracorporeal flow circuit for blood. From, for example, a fistula located in the patient's arm 35, blood is removed from the body by means of an artery needle 36 which, by means of conduit 37 and peristaltic pump 38, extends to the lower end of the dialyser 17. From the upper end of the dialyser, the conditioned blood is transferred through a conduit 29 to the drip chamber 34 where it is deaerated and returned to the patient through a conduit 40 and a venous needle 41.

The above-described flow circuit is a conventional flow circuit arranged for post-infusion. Alternatively, the conduit 33 may be connected as shown by the dashed line 41 to an inlet point 42 between the pump 38 and the dialyser 17, to thereby attain pre-infusion.

When the dialysis machine is operated for hemofiltration treatment, valve 15 is switched such that the conduit 16 is disconnected and dialyser 17 is connected to the dialysis machine solely by means of the conduit 18. In this case, dialyser 17 is exchanged for a hemofilter, which has no connector for conduit 16.

The dialysis machine comprises a computer 70 adapted to control and monitor operation of the different components of the machine. Thus, the computer operates the valves and pumps, and receives signals from valves and pumps indicating the positions and conditions thereof, as well as signals from the various meters.

During priming of the sterile filter 31, a nurse closes a conventional tube clamp 43 on tube 33 as shown in FIG. 1 and opens a conventional tube clamp 44 on the deaeration conduit 32. The dialysis solution which is pumped by the pump 29 will thus pass through the sterile filter 31 and fill it with liquid, as well as expel the air in the filter through deaeration conduit 32, which is open to the atmosphere. When all of the air has been expelled, tube clamp 44 is closed and tube clamp 43 in the conduit 33 is opened, and any air which may remain in the filter and conduit 33 passes through conduit 33 to drip chamber 34.

There are a number of errors which would be desirable to detect in such a system. For example, the nurse may forget to open the tube clamp 43 in the conduit 33 so that it is blocked at the same time that the tube clamp 44 on the conduit 32 is closed. Should this occur, the peristaltic pump 29 cannot pump any liquid or infusion solution, so that no infusion solution reaches the patient.

As a further example, if the sterile filter is not thoroughly deaerated, the infusion flow may be too low.

Should blockage or leakage in the filter arise, the situation needs to be remedied.

It is also desirable to be able to calibrate the infusion pump 29 during the treatment, or at least at the commencement of the treatment.

It is further desired to detect leakage in the pump due to the pump segment not being completely occluded.

It is also desirable to detect if an unsuitable tube set is being used, as this may result in a malfunction with resulting erroneous infusion flow.

All of these malfunctions may be detected by the present invention, as described below. It will be understood by the skilled person that operation according to the present invention may be controlled and monitored by the dialysis machine computer 70.

Figure 2:
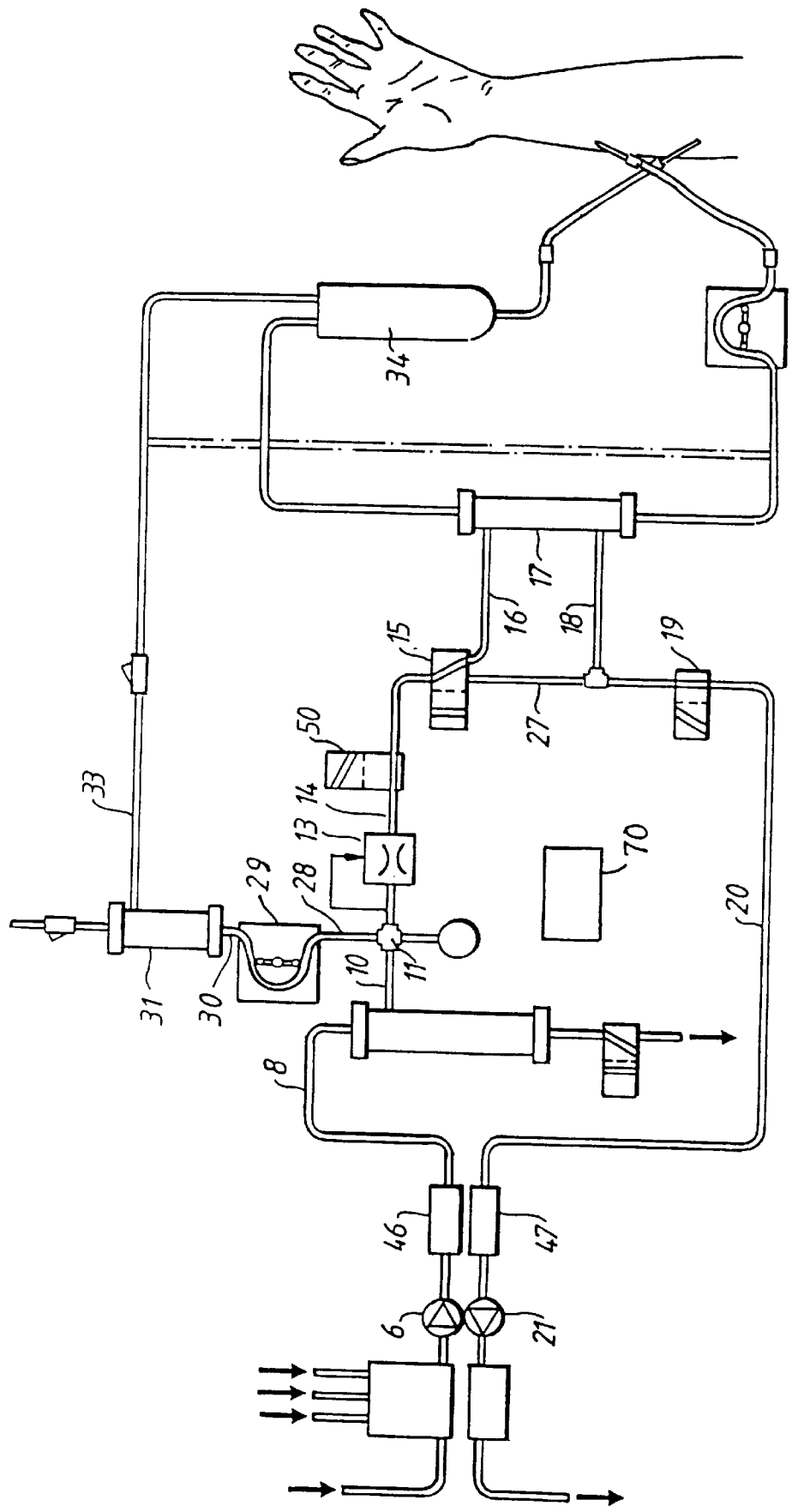
FIG. 2 is a schematic diagram corresponding to that of FIG. 1 but which has been modified in accordance with one embodiment of the invention.

According to the present invention, a cut-off valve 50 is added to the flow circuit according to FIG. 1 in the conduit 14, as shown in FIG. 2. By means of this cut-off valve 50 and valve 19, the dialyser 17 or the hemofilter may be disconnected from the dialysis circuit. The conduit 20 and the pump 21 will thereby receive zero flow.

The flow which passes through incoming channel 46 of the flow meter 7 by means of the conduits 8 and 10, and reaches the outlet 11, must pass through the infusion circuit, i.e. conduit 28, pump 29, conduit 30 and infusion filter 31, and conduit 33 to the drip chamber 34. By adjusting the dialysis machine to operate in this manner, the infusion pump 29 may be calibrated against the incoming channel 46 of the flow meter 7.

If anything should throttle the flow through the infusion circuit, this will immediately be detected by the flow meter 7, which shows zero flow despite the fact that the peristaltic pump 29 is rotating. In this manner, any incorrect priming with closed tube clamps may be detected and identified.

Possible leakage in the pump 29, such as that due to poor occlusion, may cause the flow through pump 29 to become too low or high compared to the expected flow, which may also be detected by the flow meter 7. In this case, the flow meter 7 will show a higher value than that expected from the rotational speed of the peristaltic pump 29, since there is normally a positive pressure at outlet 11.

In the same manner, an unsuitable tube set, an air-filled sterile filter, or blockage or leakage in the sterile filter can be detected as a difference between the actual measured flow through the flow meter and the expected flow based on pump rotation.

Figure 3:
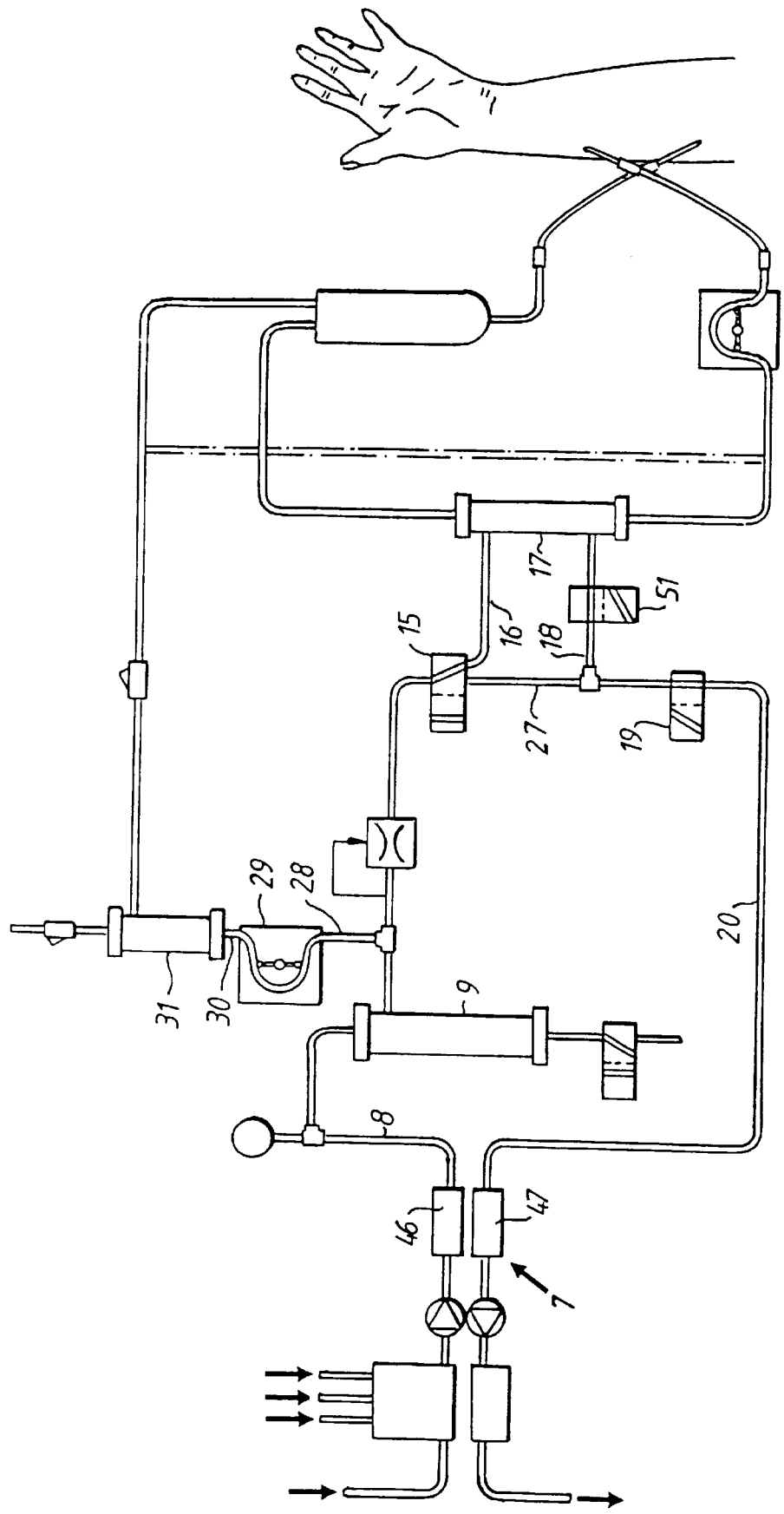
FIG. 3 is a schematic diagram corresponding to that of FIG. 1 which has been modified in accordance with another embodiment of the present invention.

All of these conditions may be detected by the dialysis machine computer 70, and the computer may then be programmed to undertake appropriate actions An alternative embodiment of the present invention is shown in FIG. 3. The valve 50 in the conduit 14 according the embodiment shown in FIG. 2 has been replaced by a valve 51 arranged in conduit 18. When activated, valve 51 closes conduit 18.

When calibration of the infusion pump 29 is to take place according to the present invention, valve 15 is switched to its second position and valve 51 is activated to its second position. In this manner, the dialyser 17 is completely disconnected. The flow in the dialysis circuit takes place through the bypass conduit 27. The flow meter 7 thus notes that the incoming flow 46 and outgoing flow 47 are equal.

If, however, the infusion pump 29 is operated at a predetermined speed, for example to achieve an expected flow rate of 50 ml/min, the incoming flow 46 through the conduit 8 will be greater than the outgoing flow 47 through the conduit 20, which is measured by the flow meter 7. In this manner, the infusion pump 29 may be calibrated with the help of the flow meter 7 by the difference between the incoming and outgoing flows in the same manner as when ultrafiltration is measured. However, the difference which is measured according to this invention will be in the other direction, which does not, however, create any problems.

A pressure meter 45 may be connected at the outlet 11. The pressure meter 45 ensures that the conditions at the outlet 11 remain the same during operation irrespective of whether the dialysis machine is connected for the calibration of the infusion pump 29.

Figure 4:
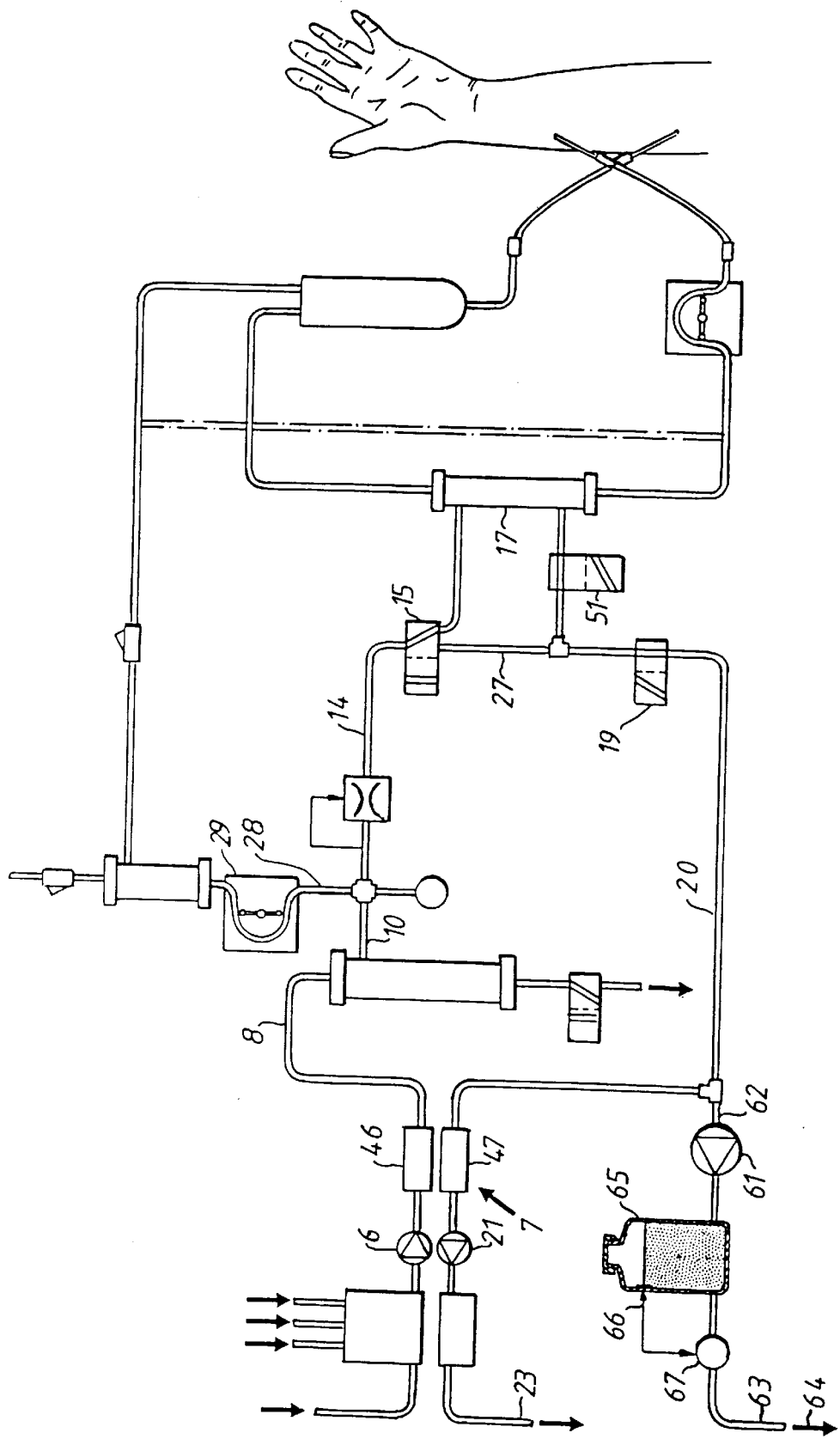
FIG. 4 is a schematic diagram corresponding to that of FIG. 1 which has been modified in accordance with another embodiment of the present invention applied to a dialysis machine with a separate ultra filtration pump.

FIG. 4 shows the present invention applied to another type of dialysis machine in which the ultrafiltrate is removed using a dedicated ultrafiltration pump 61, and in which the flow meter 7 is adjusted such that the incoming flow is always the same as the outgoing flow. Pumps 6 and 21, as well as flow meter 7, may alternatively be replaced by a so-called balancing chamber, as is well known.

Ultrafiltration pump 61 is connected to the conduit 20 by means of a conduit 62. The ultrafiltrate passes through pump 61 conduit 63 to an outlet 64. In addition, a chamber 65 is arranged in conduit 63 and is provided with a level regulator 66, 67. According to the present invention, valve 51 according to FIG. 3 is used.

When the dialysis machine according to FIG. 4 is to be used to calibrate the infusion pump 29, valve 15 is switched to its second position and valve 51 is closed so that the dialysis flow passes from the conduit 14 to the bypass conduit 27 and further to the conduit 20. In this manner, the dialyser or hemofilter 17 is isolated from the dialysis circuit. The ultrafiltration pump 61 must be stopped, since identical flows pass through the incoming and outgoing conduits of the flow meter 7.

As has been described above, a chamber 65 is connected in conduit 63 and encloses a volume of about 50 ml or more. When the infusion pump 29 is calibrated, pump 61 is reversed at the same time that the pump 29 is started. The contents in chamber 65 are pumped along conduit 20 at the same time that the pump 29 is operated. In this manner, the flow which exits through the infusion pump 29 must be as great as the flow which enters through pump 61 to conduit 20. The flow through the dialysis circuit 8, 10, 14, 27, 20 still occurs with, for example, 500 ml/min and with equal flows through the incoming conduits 46 and outgoing conduits 47.

Thus, the infusion pump 29 is calibrated against the reversed ultrafiltration pump 61. The solution which is in the chamber 65 is so-called dirty solution received from the dialyser 17. This solution will, however, be pumped into the conduit 20 and thereafter follow the flow through the flow meter 7 to the outlet 23, and thus does not affect the clean side of the dialysis circuit in conduits 8, 10 and 14.

If it is not possible to reverse the ultrafiltration pump, a valve package can be arranged instead which insures that the flow of the pump is reversed.

Calibration according to the present invention preferably takes place at the commencement of a treatment during the priming step. During this first calibration, it may be established whether the flow through the conduit 28 is far too small, in which case an alarm signal is emitted.

It is also possible to calibrate the infusion pump 29 during operation of the dialysis machine. Normally, a self-calibration of the dialysis machine takes place approximately every thirty minutes during the entire dialysis procedure. Use of the method according to the present invention may be a part of such a calibration. If the embodiment according to FIG. 2 is used, the pump 21 is connected through conduit 20, valve 19 and conduit 18 to the dialyser 17. Thus, the pump 21 can ensure that an underpressure prevails in the dialyser 17 which allows ultrafiltration to take place continuously, even during the calibration. In this embodiment, the infusion pump 29 is calibrated with respect to the incoming channel 46 of the flow meter 7.

If the embodiment according to FIG. 3 is used, the dialyser 17 is completely isolated from the dialysis machine and no ultrafiltration takes place. However, an infusion of infusion solution in the blood occurs and liquid is thus supplied to the patient. However, the supplied infusion solution is of relatively small volume, in the order of 50 ml, which can easily be compensated for by increased ultrafiltration immediately after the calibration step.

It is also to be understood that the present invention can be adapted to use with dialysis machines having conduit paths different from those described above. It is, for example, possible to use this invention in a dialysis machine which lacks the filter 9.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for monitoring an infusion pump utilized in dialysis apparatus selected from the group consisting of a dialyzer and a hemofilter comprising flowing a dialysis solution through a first flow circuit including a flow meter, flowing blood through a second flow circuit separated from said first flow circuit by a semi-permeable membrane in said dialysis apparatus, providing an infusion solution from said first flow circuit to said second flow circuit by means of an infusion pump, disconnecting said dialysis apparatus from said first flow circuit by means of an actuatable valve, and flowing a fluid through said flow meter and through said infusion pump for comparing the expected flow through said infusion pump with the measured flow through said flow meter.

2. A method of claim 1, wherein said flow meter comprises a first flow meter portion for measuring incoming flow into said first flow circuit and a second flow meter portion for measuring outgoing flow out of said first flow circuit, said first flow meter portion being connected in series with said infusion pump.

3. A method of claim 2 including flowing said fluid through said first flow circuit and bypassing said dialysis apparatus, and determining the difference between said incoming flow in said first flow meter portion and said outgoing flow in said second flow meter portion.

4. Apparatus for monitoring an infusion pump in dialysis apparatus comprising a first flow circuit for a dialysis solution, said first flow circuit including a flow meter, a second flow circuit for blood, said dialysis apparatus including a first chamber connected to said first flow circuit, a second chamber connected to said second flow circuit, and a semipermeable membrane separating said first and second chambers, a third flow circuit for withdrawing an infusion solution from said first flow circuit and delivering said infusion solution to said second flow circuit, said third flow circuit including said infusion pump, and a first valve for disconnecting said dialysis apparatus from said first flow circuit and connecting said infusion pump in series with said flow meter in said first flow circuit whereby the expected flow through said infusion pump can be compared with the measured flow through said flow meter.

5. The apparatus of claim 4, wherein said dialysis apparatus is selected from the group consisting of a dialyser and a hemofilter.

6. The apparatus of claim 4, wherein said first valve is connected in said first flow circuit upstream of said dialyser whereby when said first valve disconnects said dialysis apparatus from said first flow circuit all flow through said flow meter also passes through said infusion pump.

7. The apparatus of claim 4, wherein said flow meter comprises a first flow meter portion for measuring incoming flow with said first flow circuit and a second flow meter portion for measuring outgoing flow out of said first flow conduit, said first flow meter portion being connected in series with said infusion pump.

8. The apparatus of claim 7, wherein said first valve is located in said first flow circuit at a predetermined location for disconnecting said dialyser from said first flow circuit, and including a bypass conduit and a second valve for continuing said flow through said first flow circuit through said bypass conduit, whereby the expected flow through said infusion pump can be compared with the difference between said incoming and outgoing flows through said flow meter.

9. The apparatus of claim 8, including an ultrafiltration pump for supplying a fluid to said first flow circuit whereby the inlet flow from said ultrafiltration pump into said first flow circuit and the outlet flow out of said first flow circuit from said infusion pump can be equalized.

* * * * *